United States Patent
Ushiro et al.

(10) Patent No.: US 10,953,142 B2
(45) Date of Patent: *Mar. 23, 2021

(54) BIOLOGICAL COMPONENT ADHESION-SUPPRESSING MATERIAL

(71) Applicant: Toray Industries, Inc., Tokyo (JP)

(72) Inventors: Suguru Ushiro, Otsu (JP); Akihiro Hayashi, Otsu (JP); Yoshiyuki Ueno, Otsu (JP)

(73) Assignee: Toray Industries, Inc., Tokyo (JP)

(*) Notice: Subject to any disclaimer, the term of this patent is extended or adjusted under 35 U.S.C. 154(b) by 86 days.

This patent is subject to a terminal disclaimer.

(21) Appl. No.: 16/319,751

(22) PCT Filed: Jul. 28, 2017

(86) PCT No.: PCT/JP2017/027493
§ 371 (c)(1),
(2) Date: Jan. 22, 2019

(87) PCT Pub. No.: WO2018/025772
PCT Pub. Date: Feb. 8, 2018

(65) Prior Publication Data
US 2020/0215239 A1 Jul. 9, 2020

(30) Foreign Application Priority Data

Aug. 5, 2016 (JP) .............................. JP2016-154761

(51) Int. Cl.
*A61L 33/06* (2006.01)
*B01D 61/24* (2006.01)
*B01D 69/02* (2006.01)
*B01D 69/08* (2006.01)
*B01D 69/12* (2006.01)
*C08F 218/10* (2006.01)
*A61L 33/00* (2006.01)

(52) U.S. Cl.
CPC .......... *A61L 33/064* (2013.01); *A61L 33/007* (2013.01); *A61L 33/0041* (2013.01); *B01D 61/243* (2013.01); *B01D 69/02* (2013.01); *B01D 69/08* (2013.01); *B01D 69/12* (2013.01); *C08F 218/10* (2013.01)

(58) Field of Classification Search
CPC .. A61L 33/064; A61L 33/0041; A61L 33/007; B01D 61/243; B01D 69/02; B01D 69/08; B01D 69/12; C08F 218/10
See application file for complete search history.

(56) References Cited

U.S. PATENT DOCUMENTS

| 4,214,020 | A | * | 7/1980 | Ward | B01D 69/08 |
| | | | | | 156/180 |
| 4,720,343 | A | | 1/1988 | Walch et al. | |
| 8,394,182 | B2 | * | 3/2013 | Koros | B01D 53/228 |
| | | | | | 96/10 |
| 8,613,361 | B2 | * | 12/2013 | Ueno | B01D 71/68 |
| | | | | | 210/490 |
| 8,784,664 | B2 | | 7/2014 | Fislage et al. | |
| 10,308,745 | B2 | * | 6/2019 | Ushiro | B01D 67/0088 |
| 2008/0038307 | A1 | | 2/2008 | Hoffmann | |
| 2008/0044643 | A1 | | 2/2008 | Yokota et al. | |
| 2011/0017654 | A1 | | 1/2011 | Ueno et al. | |
| 2012/0121919 | A1 | | 5/2012 | Lindenskov | |
| 2012/0271010 | A1 | * | 10/2012 | Sakaguchi | A61L 33/0011 |
| | | | | | 525/474 |
| 2014/0158611 | A1 | | 6/2014 | Satoh et al. | |

FOREIGN PATENT DOCUMENTS

| EA | 021937 B1 | 10/2015 |
| JP | 2-18695 B2 | 4/1990 |
| JP | 6-165926 A | 6/1994 |
| JP | 6-238139 A | 8/1994 |
| JP | 2010-104984 A | 5/2010 |
| JP | 2011-173115 A | 9/2011 |
| JP | 2014-42913 A | 3/2014 |
| RU | 2026108 C1 | 1/1995 |
| RU | 2369429 C2 | 10/2009 |
| RU | 2539566 C2 | 1/2015 |
| RU | 2553430 C2 | 6/2015 |
| RU | 2556996 C1 | 7/2015 |
| SU | 1616935 A1 | 12/1990 |
| WO | 2013/015046 A1 | 1/2013 |

OTHER PUBLICATIONS

The Extended European Search Report dated Feb. 3, 2020, of counterpart European Application No. 17836877.5.
The Russian Office Action dated Jul. 21, 2020, of counterpart Russian Application No. 2019104422, along with an English translation.

* cited by examiner

*Primary Examiner* — Tae H Yoon
(74) *Attorney, Agent, or Firm* — DLA Piper LLP (US)

(57) ABSTRACT

A biological component adhesion-suppressing material includes a substrate provided with a functional layer having, fixed on a surface thereof that comes into contact with a biological component, a polymer including a saturated aliphatic monocarboxylic acid vinyl ester unit, wherein: when compositional analysis is performed on the surface of the functional layer using a TOF-SIMS device, the number of carbon atoms in an aliphatic chain representing an ion signal detected for saturated aliphatic carboxylic acid is 2-20; and an XPS measurement taken of the surface of the functional layer shows a peak derived from an ester group.

22 Claims, No Drawings

BIOLOGICAL COMPONENT ADHESION-SUPPRESSING MATERIAL

RELATED APPLICATION

This is a § 371 of International Application No. PCT/JP2017/027493, with an international filing date of Jul. 28, 2017 (WO 2018/025772 A1, published Feb. 8, 2018), which is based on JP Patent Application No. 2016-154761 filed Aug. 5, 2016.

TECHNICAL FIELD

This disclosure relates to a biological component adhesion-suppressing material, and a blood purifier including the biological component adhesion-suppressing material.

BACKGROUND

Conventional medical materials are recognized as contaminants for biological components and cause adhesion of platelets and proteins, and biological reactions, resulting in serious problems. In addition, in conventional blood purifiers such as artificial kidney modules, platelets and proteins adhere to the surfaces of materials in the blood purifier, resulting in deterioration of fractionation performance and water permeability. Particularly, in continuous blood purifiers to be used for treatment of acute renal failure, continuous use for one day to several days is required. Therefore, it is important to set specifications that ensure that adhesion of platelets and proteins is suppressed, thus making it possible to withstand use for a long period of time.

In addition, with regard to materials other than medical materials, for example, separation materials to be used for antibody purification or the like there is the problem that the recovery rate decreases due to adhesion of antibodies to the surface of the separation material. Attempts have been heretofore made to solve such a problem by hydrophilizing the surface of a medical material, and various studies have been conducted.

Japanese Patent Publication No. 2-18695 discloses a polysulfone-based polymer in which by performing molding while mixing polyvinyl pyrrolidone as a hydrophilic polymer at the stage of a membrane formation dope solution, hydrophilicity is imparted to a membrane to suppress contamination.

Japanese Patent Laid-open Publication No. 6-238139 discloses a polysulfone-based polymer separation membrane in which a coating layer insolubilized by radiation crosslinking is formed after the polymer is brought into contact with a hydrophilic polymer solution such as polyvinyl pyrrolidone.

Japanese Patent Laid-open Publication No. 2010-104984 and Japanese Patent Laid-open Publication No. 2011-173115 disclose a separation membrane of a polysulfone-based polymer in which a vinylpyrrolidone/vinyl acetate copolymer is immobilized on a surface.

Further, International Publication No. WO 2013/015046 discloses a separation membrane of a polysulfone-based polymer in which a lipid-soluble vitamin and poly (2-hydroxyalkyl methacrylate) are immobilized on a surface.

However, in the methods described in Japanese Patent Publication No. 2-18695 and Japanese Patent Laid-open Publication No. 6-238139, it is difficult to form a coating layer because of the weak interaction between a hydrophilic polymer such as polyvinyl pyrrolidone and a polysulfone-based polymer as a hydrophobic polymer. Therefore, to impart hydrophilicity to the surface by that method, it is necessary to use a large amount of a hydrophilic polymer in a membrane formation dope solution, or it is necessary to limit the hydrophilic polymer to one that is compatible with a polymer to be used as a substrate.

On the other hand, in the methods described in Japanese Patent Laid-open Publication No. 2010-104984 and Japanese Patent Laid-open Publication No. 2011-173115, a vinyl acetate unit interacts with a hydrophobic substrate to improve introduction efficiency of the copolymer so that hydrophilization can be efficiently performed, but a vinylpyrrolidone/vinyl acetate copolymer that is a commercially available polymer is used, and a structural design suitable to suppress adhesion of platelets and proteins is not considered at all. In fact, we prepared a medical material on the basis of the methods described in Japanese Patent Laid-open Publication No. 2010-104984 and Japanese Patent Laid-open Publication No. 2011-173115 and found that platelets and proteins adhered to the medical material when the medical material was in contact with blood or the like for a long period of time.

The method described in International Publication No. WO 2013/015046 is aimed at improving antioxidant performance, and has not been evaluated for antithrombogenicity. Further, a surface design associated with arrangement, immobilization and the like of a polymer is important in hydrophilization of the surface of a medical material, but this point is not described at all.

Thus, it could be helpful to provide a biological component adhesion-suppressing material that is able to suppress adhesion of platelets and proteins even when coming into contact with blood or the like.

SUMMARY

Proteins contained in blood and the like easily adhere to a hydrophobic surface and, therefore, it is important that the entire contact surface of a medical material has hydrophilicity. This may be because when protein approaches a material surface, the higher order structure of the protein is changed so that the hydrophobic site inside the protein is exposed, and the hydrophobic site hydrophobically interacts with the material surface.

On the other hand, it is known that adhesion of proteins and the like cannot be suppressed when a contact surface of a medical material is coated with a hydrophilic polymer such as polyethylene glycol or polyvinyl alcohol. This may be because when the contact surface of the medical material has excessively high hydrophilicity, the structure of protein is destabilized and, therefore, adhesion of the protein cannot be sufficiently suppressed.

We found biological component adhesion-suppressing materials that considerably suppress adhesion of platelets and proteins, and can be used even when in contact with blood or the like for a long period of time, and a blood purifier using the biological component adhesion-suppressing material. The biological component adhesion-suppressing materials and the blood purifier are as follows:

(1) A biological component adhesion-suppressing material including a substrate having a functional layer with a polymer immobilized on a surface that is in contact with a biological component, the polymer containing a saturated aliphatic monocarboxylic acid vinyl ester unit, wherein the number of carbon atoms in an aliphatic chain in a saturated aliphatic monocarboxylic acid ion signal detected in compositional analysis of the surface of the functional layer by a TOF-SIMS apparatus is 2 to 20, and a peak derived from an ester group is present in XPS measurement of the surface of the functional layer.

(2) The biological component adhesion-suppressing material according to (1), wherein the saturated aliphatic monocarboxylic acid ion signal is derived from a saturated aliphatic monocarboxylic acid vinyl ester homopolymer or a copolymer containing a saturated aliphatic monocarboxylic acid vinyl ester, and has antithrombogenicity.

(3) The biological component adhesion-suppressing material according to (1) or (2), wherein the number of carbon atoms in an aliphatic chain in the saturated aliphatic monocarboxylic acid ion signal is 2 to 9.

(4) The biological component adhesion-suppressing material according to any one of (1) to (3), wherein in XPS measurement of the surface of the functional layer, the area percentage of the carbon peak derived from an ester group is 0.5 to 25 (atomic %) where the total area of peaks derived from carbon is 100 (atomic %).

(5) The biological component adhesion-suppressing material according to any one of (1) to (4), wherein in ATR-IR measurement of the surface of the functional layer, a peak is present in each of both a range of 1711 to 1751 cm$^{-1}$ and a range of 1549 to 1620 cm$^{-1}$, and the average of the ratio of the peak area $A_{C=O}$ in the range of 1711 to 1751 cm$^{-1}$ to the peak area $A_{C=C}$ in the range of 1549 to 1620 cm$^{-1}$ ($A_{C=O}/A_{C=C}$) is 0.01 to 1.0.

(6) The biological component adhesion-suppressing material according to (5), wherein the peak present in the range of 1549 to 1620 cm$^{-1}$ is derived from aromatic groups in a polysulfone-based polymer.

(7) The biological component adhesion-suppressing material according to (5) or (6), wherein a peak is present in a range of 1617 to 1710 cm$^{-1}$ in ATR-IR measurement of the surface of the functional layer.

(8) The biological component adhesion-suppressing material according to (7), wherein the peak present in the range of 1617 to 1710 cm$^{-1}$ is derived from an amide bond in a hydrophilic polymer containing a vinylpyrrolidone unit, a vinylcaprolactam unit, a vinylacetamide unit or an acrylamide unit.

(9) The biological component adhesion-suppressing material according to any one of (1) to (8), which is used for blood purification.

(10) A blood purifier including the biological component adhesion-suppressing material according to any one of (1) to (9).

Our biological component adhesion-suppressing material can thus suppress adhesion of platelets and proteins.

DETAILED DESCRIPTION

Hereinafter, our materials will be described in detail.

Our biological component adhesion-suppressing material includes a substrate having a functional layer with a polymer immobilized on a surface that is in contact with a biological component, the polymer containing a saturated aliphatic monocarboxylic acid vinyl ester unit, wherein the number of carbon atoms in an aliphatic chain in a saturated aliphatic monocarboxylic acid ion signal detected in compositional analysis of the surface of the functional layer by a time-of-flight secondary ion mass spectrometer (hereinafter, sometimes referred to as a TOF-SIMS apparatus) is 2 to 20, and a peak derived from an ester group is present in XPS measurement of the surface of the functional layer.

"Saturated aliphatic monocarboxylic acid" means a substance including one carboxy group and a saturated aliphatic hydrocarbon group bonded to a carbon atom in the carboxy group, and examples thereof include acetic acid, propanoic acid and butyric acid.

"Saturated aliphatic" means that all carbon-carbon bonds are single bonds, and a multiple bond as in an aromatic group is not included.

"Number of carbon atoms in an aliphatic chain" means the number of carbon atoms in a saturated aliphatic hydrocarbon group bonded to a carbon atom in a carboxy group of a carboxylic acid. For example, when the number of carbon atoms in an aliphatic chain is 1, the carboxylic acid is acetic acid, and when the number of carbon atoms in an aliphatic chain is 2, the carboxylic acid is propanoic acid. When the number of carbon atoms in an aliphatic chain is small, the saturated aliphatic monocarboxylic acid has poor mobility so that adhesion of proteins and platelets easily occurs. On the other hand, when the number of carbon atoms in an aliphatic chain is large, the saturated aliphatic monocarboxylic acid has high hydrophobicity, leading to an increase in hydrophobic interaction with platelets and proteins. As a result, adhesion of platelets and proteins occurs. Therefore, in our biological component adhesion-suppressing material, the number of carbon atoms in an aliphatic chain in a saturated aliphatic monocarboxylic acid ion signal is 2 to 20, preferably 2 to 9, more preferably 2 to 5.

The saturated aliphatic hydrocarbon group may include not only a linear structure such as an ethyl group, a n-propyl group, a n-butyl group, a n-pentyl group or a n-hexyl group, but also a branched structure such as an isopropyl group or a tertiary butyl group, a cyclic structure such as a cyclopropyl group or a cyclobutyl group, and an ether bond, an ester bond or the like in the aliphatic chain. However, a structure having an anionic functional group such as a sulfonic acid group or a carboxyl group at a terminal is excluded. This is because an anionic functional group at an aliphatic chain terminal not only destabilizes the structures of platelets and proteins, and causes adhesion of the platelets and proteins to the surface of the biological component adhesion-suppressing material, but also induces undesired biological reactions such as bradykinin activation and complement activation. From the viewpoint of the production cost of the carboxylic acid, the saturated aliphatic hydrocarbon group is preferably a linear structure or a branched structure, more preferably a linear structure. Further, from the viewpoint of easy availability of the carboxylic acid and ease of polymerization, it is preferable that the saturated aliphatic hydrocarbon group is composed only of carbon atoms and hydrogen atoms.

"Biological component" means an organism-derived substance such as sugar, protein or platelet. Preferably, the biological component is a substance contained in a body fluid such as blood, tear or cerebrospinal fluid. In particular, as a target of a biological component adhesion-suppressing material having antithrombogenicity, a substance contained in blood is preferable.

"Polymer containing a saturated aliphatic monocarboxylic acid vinyl ester unit" means a saturated aliphatic monocarboxylic acid vinyl ester homopolymer, or a copolymer containing a saturated aliphatic monocarboxylic acid vinyl ester. Further, from the viewpoint of suppressing adhesion of biological components of the material, a copolymer containing a saturated aliphatic monocarboxylic acid vinyl ester is preferable. Examples of the copolymer include graft copolymers in which the branch part includes a saturated aliphatic monocarboxylic acid vinyl ester unit, and the stem part includes other units.

"Immobilization" means that a polymer is chemically or physically bonded to a substrate and the method for this is, for example, crosslinking immobilization by radiation exposure.

"Functional layer" means a layer in contact with a biological component such as blood. In, for example, an artificial kidney hollow fiber membrane, the functional layer is the inner side of the hollow fiber membrane through which blood flows.

"Substrate" refers to a component, the volume content of which is the highest of components that form the biological component adhesion-suppressing material.

"Biological component adhesion-suppressing material" means a material that suppresses adhesion of biological components to the material surface. Examples of the product in which the material is used include medical materials to be used for implantation in the body or extracorporeal circulation, separation materials to be used for purification of glycoproteins and antibodies, and analytical materials for measurement of the concentration of a component in body fluid and the like. The biological component adhesion-suppressing material means a material containing a substrate as at least a part of the material, and includes a substrate alone or a substrate immobilized on or mixed in an appropriate reinforcing material.

"Antithrombogenicity" means that adhesion of proteins and platelets among biological components is suppressed.

"Medical material" means materials used while in contact with biological components contained mainly in blood and body fluid, and examples thereof include flat membranes, hollow fiber membranes and tubes. Examples of products in which the medical material is used include blood purifiers typified by artificial kidney modules or plasma separators, which include a separation membrane, blood circuits, blood storage bags, catheters, stents and contact lenses.

Preferably, the biological component adhesion-suppressing material has antithrombogenicity. In this case, the biological component adhesion-suppressing material is preferably an antithrombotic medical material because it is excellent particularly in suppression of adhesion of proteins and platelets contained in blood and body fluid.

In the biological component adhesion-suppressing material, it is preferable that the saturated aliphatic monocarboxylic acid ion signal is derived from a saturated aliphatic monocarboxylic vinyl ester homopolymer or a copolymer containing a saturated aliphatic monocarboxylic acid vinyl ester. That is, it is preferable that the saturated aliphatic monocarboxylic acid forms an ester bond and exists as a saturated aliphatic monocarboxylic acid ester on the surface of the functional layer of the biological component adhesion-suppressing material. A carboxy group has high hydrophilicity, and destabilizes the structures of platelets and proteins. On the other hand, an ester group does not have excessively high hydrophilicity or hydrophobicity and, therefore, hardly causes adhesion of platelets and proteins. In the biological component adhesion-suppressing material, it is preferable that the saturated aliphatic monocarboxylic acid ion signal is derived from a saturated aliphatic monocarboxylic vinyl ester homopolymer or a copolymer containing a saturated aliphatic monocarboxylic acid vinyl ester, and has antithrombogenicity.

By combining compositional analysis by the TOF-SIMS apparatus and X-ray electron spectroscopy (XPS) measurement, it is possible to analyze the arrangement of the saturated aliphatic monocarboxylic acid ester at an outermost surface of about 10 nm.

First, a peak derived from a carboxylate ion of the saturated aliphatic monocarboxylic acid ester is detected by compositional analysis using the TOF-SIMS apparatus and, therefore, the structure of the carboxylic acid is revealed by analyzing the mass (m/z). In compositional analysis by the TOF-SIMS apparatus, pulsed ions (primary ions) are applied to a sample surface placed in ultrahigh vacuum, and ions (secondary ions) released from the sample surface are given certain kinetic energy, and guide to a time-of-flight mass analyzer. Each of the secondary ions accelerated with the same energy passes through the analyzer at a speed corresponding to the mass, and since the distance to the detector is constant, the time taken to reach the detector (flight time) is a function of the mass, and the distribution of the flight time is accurately measured to obtain a secondary ion mass distribution, i.e. a mass spectrum.

For example, when a secondary negative ion is detected using $Bi_3^{++}$ as primary ion species, the peak at m/z=59.02 corresponds to $C_2H_3O_2^-$, i.e. acetic acid (the number of carbon atoms in an aliphatic chain is 1). In addition, the peak at m/z=73.04 corresponds to $C_3H_5O_2^-$, i.e. propanoic acid (the number of carbon atoms in an aliphatic chain is 2).

The conditions for compositional analysis by the TOF-SIMS apparatus are as follows.

The measurement region has a size of 200 μm×200 μm, the primary ion acceleration voltage is 30 kV, and the pulse width is 5.9 nm. The detection depth in this analysis method is not more than several nanometers. When the carboxylic acid ion strength is 0.4% or less based on the total secondary ion strength, the value of the carboxylic acid ion strength is judged ascribable to noise, and it is determined that there is no carboxylic acid ion.

Further, in XPS measurement, the peak of carbon derived from an ester group (COO) appears at +4.0 to 4.2 eV from the main peak of CHx or C—C (around 285 eV) and, therefore, it is understood that the carboxylic acid forms an ester bond. A value measured at 90° as a measurement angle in XPS is used. When measurement is performed at a measurement angle of 90°, a region with a depth of about 10 nm from the surface is detected. When the ratio of the area of a peak derived from an ester group to the total area of peaks derived from carbon is 0.4% or less, the value of the area of the peak is judged as ascribable to noise, and it is determined that there is no ester group.

Combination of the above-described two results reveals whether or not the saturated aliphatic monocarboxylic acid ester is disposed on a surface of the functional layer, i.e. a surface that is in contact with a biological component.

The amount of the saturated aliphatic monocarboxylic acid ester on the surface of the functional layer of the biological component adhesion-suppressing material can be determined by measuring the amount of carbon derived from an ester group by X-ray electron spectroscopy (XPS). In the biological component adhesion-suppressing material, the area of a carbon peak derived from an ester group where the total area of peaks derived from carbon is 100 (atomic %) is preferably 0.5 to 25 (atomic %) in XPS measurement of the surface of the functional layer. To exhibit the effect of suppressing adhesion of proteins and platelets, the area ratio of the carbon peak derived from an ester group is preferably 0.5 (atomic %) or more, more preferably 1.0 (atomic %) or more, still more preferably 1.5 (atomic %) or more. On the other hand, depending on the type of biological component adhesion-suppressing material to be used, we found that the inherent performance of the biological component adhesion-suppressing material is deteriorated when the amount of the saturated aliphatic monocarboxylic acid ester is excessively large. For example, in a blood purifier such as an artificial kidney, separation performance is deteriorated when the amount of the polymer is excessively large and, therefore, the percentage of the area of a carbon peak derived from an ester group is preferably 25 (atomic %) or less, more preferably 20 (atomic %), still more preferably 10 (atomic %) or less. Any of the preferred lower limits can be combined with any of the preferred upper limits.

In XPS measurement, measurements are made at two different sites on the surface of the functional layer of the biological component adhesion-suppressing material, and an average of the values at the two sites is used. The peak of carbon derived from an ester group (COO) can be determined by peak-dividing a peak appearing at +4.0 to 4.2 eV from the main peak derived from CH or C—C in C1s. By calculating the ratio of the area of a peak derived from an ester group to the total area of peaks derived from carbon, the carbon amount (atomic %) derived from an ester group is determined. More specifically, the peak of C1s is composed of five components: a component derived mainly from CHx, C—C, C=C or C—S, a component derived mainly from C—O or C—N, a component derived from a π-π* satellite, a component derived from C=O, and a component derived from COO. The above five components are peak-divided. The component derived from COO is a peak appearing at +4.0 to 4.2 eV from the main peak of CHx or C—C (around 285 eV). The peak area ratio of each component is calculated while being rounded off from the second decimal place.

It is preferable that the polymer containing the saturated aliphatic monocarboxylic acid vinyl ester unit is immobilized on the substrate by chemical reaction or crosslinking reaction. This is aimed at preventing elution of the polymer when a biological component such as blood comes in contact with a surface of the biological component adhesion-suppressing material.

The method of immobilizing the saturated aliphatic monocarboxylic acid ester is not particularly limited, and examples thereof include a method in which a substrate and a carboxylic acid are mixed, and condensed during molding; and a method in which a substrate is immersed in a carboxylic acid or a carboxylic acid ester-containing solution, and a carboxylic acid ester is bonded by reaction caused by radiation exposure or heat. In particular, the method using a polymer containing a saturated aliphatic monocarboxylic acid vinyl ester unit in which the number of carbons in an aliphatic chain is 2 or more and 20 or less is preferably used because the polymer is introduced into the biological component adhesion-suppressing material with high efficiency, and easily disposed on the surface of the functional layer.

"Unit" refers to a repeating unit in a homopolymer or copolymer obtained by polymerizing monomers. For example, the carboxylic acid vinyl ester unit refers to a repeating unit in a homopolymer obtained by polymerizing a carboxylic acid vinyl ester monomer, or a repeating unit derived from a carboxylic acid vinyl ester monomer in a copolymer obtained by copolymerizing a carboxylic acid vinyl monomer.

For example, a polyethylene terephthalate flat membrane to be used for an artificial blood vessel or the like is immersed in an aqueous solution of a polymer, and exposed to a radiation to crosslink and immobilize the polymer. From the viewpoint of suppressing adhesion of platelets, the concentration of the aqueous solution of the polymer is preferably 0.01 ppm or more, more preferably 0.1 ppm or more. The number of adhering platelets is preferably 20 or less, more preferably 10 or less per area of $4.3 \times 10^3$ μm$^2$. The number of adhering platelets can be measured by a method as described later. In addition, in a blood circuit, it is preferable to use the blood circuit with a polymer immobilized on an inner surface of a tube or the like that forms the circuit, the inner surface being mainly in contact with blood or the like. In a catheter, stent or the like, a polymer may be immobilized on a surface of a (metal) material, which is mainly in contact with blood or the like.

Further, as a method of immobilizing the polymer containing the saturated aliphatic monocarboxylic acid vinyl ester unit on the surface of a substrate, covalent bonding by chemical reaction may be utilized. The polymer can be immobilized on the substrate surface by, for example, reacting a reactive group such as a hydroxy group, a carboxy group, an amino group, a sulfonic acid group or an alkyl halide group on the substrate surface with a reactive group introduced at the terminal of the main chain or the side chain in the polymer.

Examples of the method of introducing a reactive group to the substrate surface include a method in which a monomer having a reactive group is polymerized to obtain a substrate having a reactive group on a surface thereof; and a method in which a reactive group is introduced by ozone treatment or plasma treatment after polymerization.

Examples of the method of introducing a reactive group at the terminal of the main chain of the polymer include a method using an initiator having a reactive group such as 2,2'-azobis[2-methyl-N-(2-hydroxyethyl)propionamide] or 4,4'-azobis(4-cyanovaleric acid).

Examples of the method of introducing a reactive group to the side chain of the polymer include a method in which a monomer having a reactive group such as glycidyl methacrylate or a methacrylic acid N-hydroxysuccinimide ester is copolymerized within the bounds of not hindering the action/function of the polymer.

When the number average molecular weight of the polymer containing the saturated aliphatic monocarboxylic acid vinyl ester unit is excessively small, it may be impossible to sufficiently exhibit the effect in immobilization of the polymer on the surface of the biological component adhesion-suppressing material so that it may be difficult to suppress adhesion of platelets and proteins and, therefore, the number average molecular weight is preferably 1,000 or more, more preferably 5,000 or more. On the other hand, the upper limit of the number average molecular weight of the polymer is not particularly limited, but when the number average molecular weight is excessively large, efficiency of introduction of the polymer to the surface of the biological component adhesion-suppressing material may be deteriorated and, therefore, the number average molecular weight is preferably 1,000,000 or less, more preferably 500,000 or less, still more preferably 100,000 or less. The number average molecular weight of the homopolymer or copolymer can be measured by gel permeation chromatography (GPC) as described later.

Specific examples of the saturated aliphatic monocarboxylic acid vinyl ester homopolymer include polyvinyl propanoate, polyvinyl pivalate, polyvinyl decanoate and polyvinyl methoxyacetate, and polyvinyl propanoate (the number of carbon atoms in an aliphatic chain is 2), polyvinyl butylate (the number of carbon atoms in an aliphatic chain is 3), polyvinyl pentanoate (the number of carbon atoms in an aliphatic chain is 4), polyvinyl pivalate (the number of carbon atoms in an aliphatic chain is 4) and polyvinyl hexanoate (the number of carbon atoms in an aliphatic chain is 5) are preferable because they do not have excessively high hydrophobicity.

The monomer to be copolymerized with the saturated aliphatic monocarboxylic acid vinyl ester is not particularly limited, and examples thereof include hydrophobic monomers typified by alkyl methacrylate-based monomers, alkyl acrylate-based monomers, styrene-based monomers and the like; and hydrophilic monomers typified by vinyl alcohol monomers, acryloyl morpholine monomers, vinyl pyridine-based monomers, vinyl imidazole-based monomers, vinyl pyrrolidone monomers and the like. It is preferable to copolymerize a hydrophilic monomer from the viewpoint of controlling the hydrophilicity of the entire copolymer. In particular, monomers having an amide bond, an ether bond or an ester bond are preferable because they do not have excessively high hydrophilicity, and are more easily balanced with a hydrophobic monomer as compared to monomers having a carboxy group or a sulfonic acid group. Particularly, vinylacetamide monomers having an amide bond, vinylpyrrolidone monomers and vinylcaprolactam monomers are more preferable. Among them, vinylpyrrolidone monomers are still more preferable because the polymer has low toxicity. Examples of the copolymer containing a carboxylic acid vinyl ester include vinyl alcohol/vinyl pentanoate copolymers and vinyl pyrrolidone/vinyl hexanoate copolymers.

Here, "hydrophilic monomer" is defined as a monomer, the homopolymer of which is easily soluble in water. Here, "easily soluble in water" means that the solubility in 100 g of pure water at 20° C. is more than 1 g, preferably 10 g or more.

From the viewpoint of suppression of adhesion of biological components by the biological component adhesion-suppressing material, the molar fraction of the saturated aliphatic monocarboxylic acid vinyl ester in the entire copolymer containing the saturated aliphatic monocarboxylic acid vinyl ester is preferably 10% or more and 90% or less, more preferably 20% or more and 80% or less. When the molar fraction is excessively large, the hydrophobicity of the entire copolymer increases so that adhesion of proteins and platelets easily occurs. On the other hand, when the molar fraction is excessively small, the hydrophilicity of the entire copolymer may increase to cause structure destabilization/denaturation of platelets and proteins, leading to occurrence of adhesion. As a method of calculating the molar fraction, for example, nuclear magnetic resonance (NMR) measurement is performed, and the molar fraction is calculated from a peak area. When the molar fraction cannot be calculated by NMR measurement because peaks overlap each other, the molar fraction may be calculated by elemental analysis.

Other monomers, e.g. monomers containing a reactive group such as a hydroxy group, a carboxy group or glycidyl group may be copolymerized within the bounds of not hindering the action/function of the polymer containing the saturated aliphatic monocarboxylic acid vinyl ester.

As a sequence of units in the copolymer containing the saturated aliphatic monocarboxylic acid vinyl ester, mention is made of, for example, a block copolymer, an alternating copolymer, a random copolymer or the like. Among them, an alternating copolymer or random copolymer is preferable because the copolymer as a whole has a small distribution of hydrophilicity/hydrophobicity. In particular, a random copolymer is more preferable because synthesis is not complicated. A copolymer in which at least a part of the monomer sequence is unordered is a random copolymer.

The polymer containing the saturated aliphatic monocarboxylic acid vinyl ester unit can be synthesized by a chain polymerization method typified by, for example, a radical polymerization method using an azo-based initiator, but the synthesis method is not limited thereto.

The polymer containing the saturated aliphatic monocarboxylic acid vinyl ester unit is produced by, for example, the following production method, but the production method is not limited to thereto.

A saturated aliphatic monocarboxylic acid vinyl ester monomer, a polymerization solvent and a polymerization initiator are mixed, and the mixture is mixed with stirring in a nitrogen atmosphere at a predetermined temperature for a predetermined period of time to carry out polymerization reaction. If necessary, copolymerization with a hydrophilic monomer or a hydrophobic monomer is performed. The reaction liquid is cooled to room temperature to stop the polymerization reaction, and is put in a solvent such as hexane. The deposited precipitate is recovered, and dried under reduced pressure to obtain a polymer containing a carboxylic acid vinyl ester unit.

The reaction temperature of the polymerization reaction is preferably 30 to 150° C., more preferably 50 to 100° C., still more preferably 70 to 80° C.

The pressure of the polymerization reaction is preferably atmospheric pressure.

The reaction time of the polymerization reaction is appropriately selected according to conditions such as a reaction temperature, but is preferably 1 hour or more, more preferably 3 hours or more, still more preferably 5 hours or more. When the reaction time is short, a large amount of an unreacted monomer may be apt to remain in the polymer. On the other hand, the reaction time is preferably 24 hours or less, more preferably 12 hours or less. When the reaction time is long, side reactions such as production of a dimer formation may easily occur, thus making it difficult to control the molecular weight.

The polymerization solvent to be used in the polymerization reaction is not particularly limited as long as it is a solvent compatible with a monomer and, for example, an ether-based solvent such as dioxane or tetrahydrofuran, an amide-based solvent such as N,N-dimethylformamide, a sulfoxide-based solvent such as dimethylsulfoxide, an aromatic hydrocarbon-based solvent such as benzene or toluene, an alcohol-based solvent such as methanol, ethanol, isopropyl alcohol, amyl alcohol or hexanol, water or the like is used, but from the viewpoint of toxicity it is preferable to use an alcohol-based solvent or water.

As the polymerization initiator for the polymerization reaction, for example, a photopolymerization initiator or a thermal polymerization initiator is used. A polymerization initiator that generates any of a radical, a cation and an anion may be used, but a radical polymerization initiator is preferably used because it does not cause decomposition of a monomer. As the radical polymerization initiator, for example, an azo initiator such as azobisisobutyronitrile, azobisdimethylvaleronitrile or dimethyl azobis(isobutyrate), or a peroxide initiator such as hydrogen peroxide, benzoyl peroxide, di-tert-butyl peroxide or dicumyl peroxide is used.

The solvent in which a polymerization reaction is put after polymerization reaction is stopped is not particularly limited as long as it is a solvent in which the polymer is precipitated and, for example, a hydrocarbon-based solvent such as pentane, hexane, heptane, octane, nonane or decane, or an ether-based solvent such as dimethyl ether, ethyl methyl ether, diethyl ether or diphenyl ether is used.

The polymer to be used as a substrate is not particularly limited, and examples thereof include polysulfone-based polymers, polystyrene, polyurethane, polyethylene, polypropylene, polycarbonate, polyvinylidene fluoride, polyacrylonitrile, polymethyl methacrylate, polyvinyl chloride and polyester. In particular, it is preferable that the polymer to be used as a substrate has an aromatic group from the viewpoint of imparting sufficient strength to the biological component adhesion-suppressing material. Particularly, the polysulfone-based polymer is preferably used because a flat membrane or a hollow fiber membrane is easily formed, and a polymer containing the saturated aliphatic monocarboxylic acid vinyl ester unit is easily applied.

The immobilization amount of the polymer containing the saturated aliphatic monocarboxylic acid vinyl ester unit on the surface of the functional layer of the biological component adhesion-suppressing material can also be quantitatively determined by total reflection infrared spectroscopy (ATR-IR). In ATR-IR, it is possible to perform measurement in compositional analysis up to a depth of several micrometers from the surface.

When the surface of the functional layer of the biological component adhesion-suppressing material includes a polymer containing a saturated aliphatic monocarboxylic acid vinyl ester unit, an infrared absorption peak derived from an ester group C=O appears in a range of 1711 to 1751 $cm^{-1}$. In addition, when the substrate is composed of a polymer having an aromatic group, an infrared absorption peak derived from an aromatic group C=C appears in a range of 1549 to 1620 $cm^{-1}$. In the biological component adhesion-suppressing material, it is preferable that a peak present in a range of 1549 to 1620 $cm^{-1}$ is preferably derived from an aromatic group in a polysulfone-based polymer. The reason why a polysulfone-based polymer is preferable is as described below.

In quantitative determination of the surface immobilization amount of a polymer containing a saturated aliphatic monocarboxylic acid vinyl ester unit by ATR-IR, the ratio of the area ($A_{C=O}$) of an infrared absorption peak derived from an ester group C=O at 1711 to 1751 $cm^{-1}$ to the area ($A_{C=C}$) of an infrared absorption peak derived from an aromatic group C=C at 1549 to 1620 $cm^{-1}$ ($A_{C=O}/A_{C=C}$) is measured at three arbitrary sites on the surface of the functional layer of one biological component adhesion-suppressing material, and the average thereof is defined as a surface immobilization amount of the polymer.

In the biological component adhesion-suppressing material, it is preferable that in ATR-IR measurement of the surface of the functional layer, a peak is present in each of both a range of 1711 to 1751 $cm^{-1}$ and a range of 1549 to 1620 $cm^{-1}$, and the average of the ratio of the peak area $A_{C=O}$ in the range of 1711 to 1751 $cm^{-1}$ to the peak area $A_{C=C}$ in the range of 1549 to 1620 $cm^{-1}$ ($A_{C=O}/A_{C=C}$) is 0.01 to 1.0. To sufficiently suppress adhesion of proteins and platelets to the biological component adhesion-suppressing material, the surface immobilization amount of the polymer containing a saturated aliphatic monocarboxylic acid vinyl ester unit, i.e. the average of ($A_{C=O}/A_{C=C}$) is preferably 0.01 or more, more preferably 0.02 or more, still more preferably 0.03 or more. The upper limit of the surface immobilization amount of the polymer containing a saturated aliphatic monocarboxylic acid vinyl ester unit is not particularly limited, but when the surface immobilization amount of the polymer is excessively large, the amount of an eluate may increase and, therefore, the surface immobilization amount of the polymer is preferably 1.0 or less, more preferably 0.9 or less, still more preferably 0.8 or less. Any of the preferred lower limits can be combined with any of the preferred upper limits. However, when the surface immobilization amount is 0.005 or less, the value of the surface immobilization amount is judged ascribable to noise, and it is determined that there is not a polymer containing a carboxylic acid vinyl ester unit.

Examples of the polymer having the aromatic group include polysulfone-based polymers, polystyrene, polyester and polyamide. Among them, polysulfone-based polymers are preferably used because a flat membrane or a hollow fiber membrane is easily formed, and a polymer containing the saturated aliphatic monocarboxylic acid vinyl ester unit is easily applied. The above-described method is a quantitative determination method where the substrate is a polymer having an aromatic group, and when the substrate is composed of a different material, another peak may be appropriately selected to perform calculation.

The substrate having an aromatic group generally has high hydrophobicity and, therefore, may contain a hydrophilic polymer.

Preferably, the hydrophilic polymer contains an amide bond because it does not have extremely high hydrophilicity.

Examples of the hydrophilic polymer containing an amide bond include hydrophilic polymers obtained by (co)polymerizing vinyl caprolactam, vinyl pyrrolidone, vinyl acetamide, acrylamide or a derivative thereof. Among them, a hydrophilic polymer obtained by polymerizing vinyl pyrrolidone is preferably used because it has favorable moldability and spinnability with a polymer having an aromatic group such as a polysulfone-based polymer, and also serves as a pore forming agent in formation of a hollow fiber membrane.

Here, "hydrophilic polymer" is defined as a polymer easily soluble in water. Here, "easily soluble in water" means that the solubility in 100 g of pure water at 20° C. is more than 1 g, preferably 10 g or more.

Presence of a hydrophilic polymer containing an amide bond on the surface of the biological component adhesion-suppressing material can be confirmed by observing a peak of 1617 to 1710 $cm^{-1}$ in ATR-IR measurement. That is, in the biological component adhesion-suppressing material, it is preferable that a peak is 1617 to 1710 $cm^{-1}$ in ATR-IR measurement of the surface of the functional layer. In addition, in the biological component adhesion-suppressing material, it is preferable that a peak of 1617 to 1710 $cm^{-1}$ is derived from an amide bond in a hydrophilic polymer containing a vinylpyrrolidone unit, a vinylcaprolactam unit, a vinylacetamide unit or an acrylamide unit. The reason why it is preferable that a peak present of 1617 to 1710 $cm^{-1}$, i.e. an amide bond is contained or the amide bond is derived from each of the above-mentioned units is as described above.

As an abundance of the hydrophilic polymer containing an amide bond on the surface of the biological component adhesion-suppressing material, the ratio of the area ($A_{N-C=O}$) of a peak derived from the amide bond to the area ($A_{C=C}$) of a peak of the aromatic group ($A_{N-C=O}/A_{C=C}$) is measured at three arbitrary sites on the surface of the functional layer of one biological component adhesion-suppressing material, and the average thereof is defined as the abundance of the hydrophilic polymer. The abundance of the hydrophilic polymer, i.e. the average of ($A_{N-C=O}/A_{C=C}$) is preferably 0.01 or more, more preferably 0.1 or more, still more preferably 0.5 or more. In addition, there is no particular upper limit on the abundance of the hydrophilic polymer, when the amount of the hydrophilic units is excessively large, the amount of the eluate from the surface of the biological component adhesion-suppressing material may increase and, therefore, the average of the abundance ($A_{N-C=O}/A_{C=C}$) is preferably 50 or less, more preferably 10 or less, still more preferably 5 or less. Any of the preferred lower limits can be combined with any of the preferred upper limits. However, when the average value of ($A_{N-C=O}/A_{C=C}$) is 0.005 or less, the value of the average of the abundance is judged ascribable to noise, and it is determined that there is not a hydrophilic polymer containing an amide bond.

In addition, a blood purifier includes the biological component adhesion-suppressing material.

For example, the blood purifier may be a separation membrane formed such that as one component for forming a separation membrane as one form of the biological component adhesion-suppressing material, the polymer is immobilized on a surface of the membrane (particularly, an inner surface frequently brought into blood) to suppress adhesion of blood components, and the separation membrane is included in a casing. The form of the separation membrane is preferably a hollow fiber membrane from the viewpoint of blood purification efficiency.

"Use for blood purification" means that a product is used for the purpose of removing wastes and harmful substances in blood.

"Blood purifier" refers to a product having in at least a part thereof a medical material aimed at removing wastes and harmful substances in blood by circulating blood outside the body, and examples thereof include artificial kidney modules and exotoxin adsorption columns.

The blood purifier is used while being in contact with blood for a long period of time, e.g. about 4 hours in the case of an artificial kidney module used for treatment of chronic renal failure and 1 day to several days for a continuous blood filter used for treatment of acute renal failure. Thus, adhesion of platelets and proteins occurs, resulting in deterioration of fractionation performance and water permeability. Further, since the artificial kidney module and the continuous blood filter are subjected to filtration from the inside to the outside of the hollow fiber membrane for removing wastes and harmful substances in blood, adhesion of platelets and proteins particularly easily occurs.

"Separation membrane" means a membrane that selectively removes a specific substance contained in a liquid to be treated such as blood or an aqueous solution by adsorption or on the basis of the size of a substance. As a method of producing the separation membrane, for example, a method in which a membrane is formed, and then coated with a polymer is preferable, and a method in which a polymer in the form of a solution (preferably an aqueous solution) is brought into contact with a surface of the film is used. More specific examples include a method in which a polymer solution is caused to flow at a predetermined flow rate, and a method in which a membrane is immersed in the solution. In addition, mention is also made of a method in which conditions are set so that a polymer is intentionally put together on a membrane surface in a method in which a polymer is added to a dope solution for forming a membrane, and the mixture is spun.

The main raw material of the separation membrane is preferably a polysulfone-based polymer. "Polysulfone-based polymer" is a polymer having an aromatic ring, a sulfonyl group and an ether group in the main chain, and examples thereof include polysulfone, polyether sulfone and polyaryl ether sulfone. "Main raw material" means a raw material contained in an amount of 90% by weight or more based on the total of the polysulfone-based polymer.

As the main raw material of the separation membrane, for example, a polysulfone-based polymer represented by the chemical formula of formula (1) and/or (2) is preferably used, but the main raw material of the separation membrane is not limited thereto. In the formula, n is an integer of 1 or more, preferably 30 to 100, more preferably 50 to 80. When n has a distribution, the average of the distribution is defined as n.

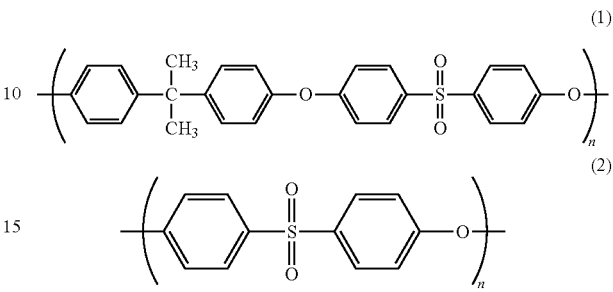

In the formulae, n represents an integer of 1 or more.

The polysulfone-based polymer that can be used for the separation membrane module is preferably a polymer composed only of a repeating unit represented by formula (1) and/or (2), but may be a copolymer obtained by copolymerization with a monomer other than the monomer derived from the repeating unit represented by formula (1) and/or (2), or a modified product thereof. The copolymerization ratio of the above-mentioned other monomer in the copolymer obtained by copolymerization with the above-mentioned other monomer is preferably 10% by weight or less based on the total of the polysulfone-based polymer.

Examples of the polysulfone-based polymer that can be used for the separation membrane module include polysulfone-based polymers such as Udel Polysulfone P-1700 and P-3500 (manufactured by Solvay), ULTRASON (registered trademark) S3010 and S6010 (manufactured by BASF SE), VICTREX (manufactured by Sumitomo Chemical Co., Ltd.), RADEL (registered trademark) A (manufactured by Solvay) and ULTRASON (registered trademark) E (manufactured by BASF SE).

There are various methods of producing the separation membrane module depending on the use of the separation membrane module and, as one aspect thereof, the method can be divided into a step of producing a separation membrane and a step of incorporating the separation membrane into a module. In production of the separation membrane module, treatment by radiation exposure may be performed before the step of incorporating the separation membrane into a module, or may be performed after the step of incorporating the separation membrane into a module. When the separation membrane module is a separation membrane module for medical use, it is preferable to perform treatment by γ ray irradiation as treatment by radiation exposure after the step of incorporating the separation membrane into a module because sterilization can be performed at the same time.

One example of a method of producing a hollow fiber membrane module to be used in a blood purifier will be described.

Examples of the method of producing a hollow fiber membrane to be incorporated into a blood purifier include the following method. That is, polysulfone and polyvinylpyrrolidone (weight ratio of preferably 20:1 to 1:5, more preferably 5:1 to 1:1) is dissolved in a mixed solvent of a good solvent (preferably N,N-dimethylacetamide, dimethylsulfoxide, N,N-dimethylformamide, N-methylpyrrolidone, dioxane or the like) and a poor solvent (preferably water, ethanol, methanol, glycerin or the like) for polysulfone to obtain a dope solution (concentration of preferably 10 to 30% by weight, more preferably 15 to 25% by weight), and at the time of discharging the dope solution from a double ring-shaped die, a bore fluid is fed to the inside, and the dope solution is run through a dry section, and then guided to a coagulation bath. Since the humidity of the dry section affects the dope solution, the phase separation behavior in the vicinity of the outer surface is accelerated by supplying moisture from the outer surface of the membrane during running of the dry section so that the pore diameter can be increased, resulting in reduction of permeation/diffusion resistance in dialysis. However, when the relative humidity is excessively high, coagulation of the dope solution on the outer surface is dominant so that the pore diameter tends to rather decrease, resulting in increase of permeation/diffusion resistance in dialysis. Therefore, the relative humidity is preferably 60 to 90%. In addition, it is preferable to use a bore fluid having a composition based on the solvent used for the dope solution from the viewpoint of process suitability. For example, when N,N-dimethylacetamide is used, an aqueous solution with a bore fluid concentration of preferably 45 to 80% by weight, more preferably 60 to 75% by weight is used.

Good solvent means a solvent in which a target polymer is soluble in an amount of 10% by weight or more at 20° C. Poor solvent means a solvent in which a target polymer is soluble in an amount of less than 10% by weight at 20° C.

The method of incorporating the hollow fiber membrane into the module is not particularly limited, and examples thereof include the following method. First, the hollow fiber membrane is cut to a required length, and a required number of pieces are bundled, and placed in a cylindrical case. Both ends of the case are then temporarily capped, and a potting agent is placed at both ends of the hollow fiber membrane. A method in which the potting agent is placed while the module is rotated with a centrifuge is a preferred method because the potting agent is uniformly packed. After the potting agent is solidified, the hollow fiber membrane is cut at both end portions to be opened at both ends so that a hollow fiber membrane module is obtained.

The polysulfone-based polymer used as a main raw material of the hollow fiber membrane generally has high hydrophobicity and, therefore, when the polysulfone-based polymer is used as a hollow fiber membrane as it is, adhesion of organic substances such as proteins easily occurs. Thus, a hollow fiber membrane in which a polymer containing the carboxylic acid ester unit is immobilized on the surface of a functional layer is preferably used. In particular, from the viewpoint of improving the hydrophilicity of the surface of the functional layer, a polymer containing a carboxylic acid ester unit copolymerized with the hydrophilic unit is preferably used. Examples of the method of introducing the polymer to the surface of the functional layer include a method in which a solution of the polymer is brought into contact with a hollow fiber membrane in the module: and a method in which at the time of spinning the hollow fiber membrane, a bore fluid containing the polymer is brought into contact with the inside of the hollow fiber membrane.

When an aqueous solution of the polymer containing the saturated aliphatic monocarboxylic acid vinyl ester unit is fed through the hollow fiber membrane in the module and introduced to the surface, a sufficient amount of the polymer is not introduced to the surface when the concentration of the polymer in the aqueous solution is excessively low. Therefore, the polymer concentration in the aqueous solution is preferably 10 ppm or more, more preferably 100 ppm or more, still more preferably 300 ppm or more. When the concentration of the polymer in the aqueous solution is excessively large, the amount of an eluate from the module may increase and, therefore, the polymer concentration in the aqueous solution is preferably 100,000 ppm or less, more preferably 10,000 ppm or less.

When the polymer containing the saturated aliphatic monocarboxylic acid vinyl ester unit is not dissolved in water at a predetermined concentration, the polymer may be dissolved in a mixed solvent of water and an organic solvent in which the hollow fiber membrane is insoluble, or an organic solvent which is compatible with water and in which the hollow fiber membrane is insoluble. Examples of the organic solvent that can be used for the organic solvent or the mixed solvent include, but are not limited to, alcohol-based solvents such as methanol, ethanol and propanol.

In addition, when the ratio of the organic solvent in the mixed solvent increases, the hollow fiber membrane may be swollen, leading to reduction of strength. Therefore, the weight fraction of the organic solvent in the mixed solvent is preferably 60% or less, more preferably 10% or less, still more preferably 1% or less.

Further, from the viewpoint of improving the hydrophilicity of the hollow fiber membrane as a whole, it is preferable that a polysulfone-based polymer and a polymer containing a hydrophilic unit are mixed, and the mixture is spun.

To prevent elution of the polymer containing the introduced carboxylic acid vinyl ester unit at the time of use, it is preferable that after being introduced to the surface of the biological component adhesion-suppressing material, the polymer is subjected to radiation exposure or thermal treatment to be insolubilized so that the polymer is immobilized on the surface of the biological component adhesion-suppressing material.

For the radiation exposure, an $\alpha$-ray, a $\beta$-ray, a $\gamma$-ray, an X-ray, an ultraviolet ray, an electron beam or the like can be used. Blood purifiers such as artificial kidneys are obliged to be sterilized prior to shipping and, in recent years, a radiation sterilization method using a $\gamma$ ray or an electron beam has been heavily used from the viewpoint of the low residual toxicity and convenience. Therefore, it is preferable that a radiation sterilization method is used while an aqueous solution in which a polymer is dissolved is in contact with the hollow fiber membrane in the medical separation membrane module because insolubilization of the polymer can be achieved in parallel to sterilization.

When the hollow fiber membrane is sterilized and reformed at the same time in the biological component adhesion-suppressing material, the irradiation dose of a radiation is preferably 15 kGy or more, more preferably 25 kGy or more. This is because an irradiation dose of 15 kGy or more is effective for sterilizing a blood purification module or the like with a $\gamma$-ray. In addition, the irradiation dose is preferably 100 kGy or less. This is because when the irradiation dose is more than 100 kGy, the polymer may easily undergo three-dimensional crosslinking, decomposition of the ester group moiety in the carboxylic acid vinyl ester unit, or the like, leading to deterioration of blood compatibility.

An antioxidant may be used to suppress a crosslinking reaction in radiation exposure. The antioxidant means a substance having a property of easily giving electrons to other molecules, and examples thereof include, but are not limited to, water-soluble vitamins such as vitamin C, polyphenols, and alcohol-based solvents such as methanol, ethanol and propanol. These antioxidants may be used singly, or in combination of two or more thereof. When an antioxidant is used for the medical separation membrane module, it is necessary to take safety into consideration and, therefore, an antioxidant having low toxicity such as ethanol or propanol is preferably used.

In a blood purifier such as an artificial kidney module, not only fractionation performance and permeability may be deteriorated due to adhesion of proteins and platelets, but also it may be impossible to continue extracorporeal circulation because blood cannot flow into the hollow fiber membrane due to blood coagulation. Adhesion of platelets and proteins to the inside of the hollow fiber membrane occurs markedly within 60 minutes after the membrane comes into contact with blood and, therefore, the performance of the hollow fiber membrane can be evaluated by measuring the relative adhesion amount of fibrinogen to the inner surface of the hollow fiber membrane after circulation of blood for 60 minutes.

Blood coagulation and activation of blood components are said to start with adhesion of fibrinogen to the surface of the biological component adhesion-suppressing material as an initiation point, i.e. it can be said that the smaller the adhesion amount of fibrinogen, the higher the antithrombogenicity of the biological component adhesion-suppressing material.

The adhesion amount of fibrinogen to the hollow fiber membrane can be measured by a method as described later. To prevent blood-dependent variations in the adhesion amount of fibrinogen, measurement of the hollow fiber membrane in Artificial Kidney "Toraylight" CX manufactured by Toray Industries, Inc. is performed in parallel as a control, and the adhesion amount relative to the control is calculated.

"Having antithrombogenicity" means that the relative adhesion amount of fibrinogen is 90% or less, preferably 55% or less. From the viewpoint of suppressing blood coagulation and activation of blood components, the relative adhesion amount of fibrinogen to the biological component adhesion-suppressing material is preferably 25% or less, more preferably 20% or less, still more preferably 15% or less.

On the other hand, the biological component adhesion-suppressing material can also be used for separation materials and analytical materials. Examples of the separation material include antibody purifying separation membranes. The antibody purifying separation membrane is used to remove impurities such as undesired proteins to purify antibodies such as IgG, IgM, IgA, IgD and IgE from serum, ascites or a cell culture medium, and has the problem that antibodies adhere to the separation film surface, resulting in reduction of the recovery rate. By using the biological component adhesion-suppressing material, reduction of the recovery rate can be suppressed. For example, in purification of IgG, the recovery rate depends on the method of using the separation membrane, but is preferably 50% or more, more preferably 55% or more, still more preferably 60% or more from the viewpoint of cost.

Examples of the analytical material include blood glucose level sensors. The blood glucose level sensor measures the glucose concentration in body fluid such as serum, and has the problem that proteins in body fluid adhere to a sensor element surface so that it is impossible to recognize glucose, resulting in reduction of the sensitivity. By using the biological component adhesion-suppressing material reduction of the sensitivity can be suppressed.

EXAMPLES

Our materials will be illustrated below with reference to Examples, but it should be understood that this disclosure is not construed as being limited thereto.

Evaluation Method (1) Number Average Molecular Weight

A 0.1 N $LiNO_3$ solution of water/methanol=50/50 (volume ratio) was prepared and used as a GPC development solution. 2 mg of the polymer was dissolved in 2 ml of this solution. 100 µL of the polymer solution was injected into a GPC connected to a column (Tosoh $GMPW_{XL}$). The flow rate was 0.5 mL/min, and the measurement time was 30 minutes. Detection was performed using a differential refractive index detector RID-10A (manufactured by Shimadzu Corporation) and the number average molecular weight calculated from a peak derived from the polymer, which appeared around an elution time of 15 minutes. The number average molecular weight was calculated while being rounded off from the tenth decimal place. A polyethylene oxide standard sample (0.1 kD to 1258 kD) manufactured by Agilent Company was used for preparation of a calibration curve.

(2) Molar Fraction of Carboxylic Acid Vinyl Ester Unit 2 mg of the copolymer was dissolved in 2 ml of chloroform-D (99.7%) (Wako Pure Chemical Industries, Ltd., 0.05V/V %, with TMS), and the solution added in a NMR sample tube, and subjected to NMR measurement (superconducting FTNMR EX-270: manufactured by JEOL Ltd.). The temperature was room temperature, and the cumulative number was 32. From the result of this measurement, the value of $A_{VC}/(A_{PVP}+A_{VC}) \times 100$ was calculated as a molar fraction of the carboxylic acid vinyl ester unit where the area of a region surrounded by a base line and a peak observed in a range of 2.7 to 4.3 ppm and derived from a proton (3H) bonded to a carbon atom adjacent to a nitrogen atom in vinyl pyrrolidone is $3A_{PVP}$, and the area of a region surrounded by a base line and a peak observed in a range of 4.3 to 5.2 ppm and derived from a proton (1H) bonded to carbon at the α-position in the carboxylic acid vinyl ester is Avg. This method is an example of measuring the molar fraction in a copolymer of vinyl pyrrolidone and a carboxylic acid vinyl ester, and in a copolymer including a combination of other monomers, an appropriate proton-derived peak is selected and the molar fraction determined. The molar fraction was calculated while being rounded off from the ones place.

(3) TOF-SIMS Measurement

In a hollow fiber membrane, the membrane was trimmed and cut to a half-cylindrical shape with a single edge, and measurement performed at three different sites on a surface (inside surface) of the functional layer of the hollow fiber membrane. In a membrane other than a hollow fiber membrane such as a flat membrane, the surface of the functional layer was exposed if necessary, and measurement was performed at three different sites on the surface of the functional layer. The measurement sample was rinsed with ultrapure water, then dried at room temperature and 0.5 Torr for 10 hours, and then subjected to measurement. The measurement apparatus and conditions are as follows.

Measurement apparatus: TOF. SIMS 5 (manufactured by ION-TOF Company)
Primary ion: $Bi_3^{++}$
Primary ion acceleration voltage: 30 kV
Pulse width: 5.9 ns
Secondary ion polarity: negative
Number of scans: 64 scan/cycle
Cycle time: 140 µs Measurement range: 200×200 μm$^2$
Mass range (m/z): 0 to 1500

From the obtained mass m/z spectrum, whether or not carboxylic acid ions are present on the surface of the biological component adhesion-suppressing material was examined. When the carboxylic acid ion strength is 0.4% or less based on the total secondary ion strength, the value of the carboxylic acid ion strength is judged ascribable to noise, and determined that there is no carboxylic acid.

(4) X-Ray Electron Spectroscopy (XPS) Measurement

In a hollow fiber membrane, the membrane was trimmed and cut to a semi-cylindrical shape with a single-edged blade, and measurement performed at two different sites on a surface (inside surface) of the functional layer of the hollow fiber membrane. In a membrane other than a hollow fiber membrane such as a flat membrane, the surface of the functional layer was exposed if necessary, and measurement performed at two different sites on the surface of the functional layer. The measurement sample was rinsed with ultrapure water, then dried at room temperature and 0.5 Torr for 10 hours, and then subjected to measurement. The measurement apparatus and conditions are as follows.

Measurement apparatus: ESCALAB 220i XL (manufactured by VG Corporation)
Excited X-ray: monochromatic Al Kα 1,2 ray (1486.6 eV)
X-ray diameter: 0.15 mm
Photoelectron escape angle: 90° (inclination of a detector with respect to a sample surface)

The peak of C1s is composed of five components: a component derived mainly from CHx, C—C, C=C or C—S, a component derived mainly from C—O or C—N, a component derived from a π-π* satellite, a component derived from C=O, and a component derived from COO. The above five components are peak-divided. The component derived from COO is a peak appearing at +4.0 to 4.2 eV from the main peak of CHx or C—C (around 285 eV). The peak area ratio of each component was calculated while being rounded off from the second decimal place. When the peak area percentage was 0.4% or less as a result of peak division, the peak was considered undetectable.

(5) ATR-IR Measurement

The hollow fiber membrane was trimmed and cut to a semi-cylindrical shape with a single-edged blade, rinsed with ultrapure water, and then dried at room temperature and 0.5 Torr for 10 hours to prepare a surface measuring sample. In a membrane other than a hollow fiber membrane such as a flat membrane, the surface of the functional layer was exposed if necessary, rinsed with ultrapure water, and then dried at room temperature and 0.5 Torr for 10 hours to prepare a surface measuring sample. The surface of the functional layer of the dried sample was measured by a microscopic ATR method using IRT-3000 manufactured by JASCO Corporation. The measurement was performed with the visual field (aperture) set to 100 μm×100 μm, the measurement range set to 3 μm×3 μm and the cumulative number set to 30. A reference line was drawn at a wavelength of 1549 to 1620 cm$^{-1}$ in the obtained spectrum, and the area of a portion surrounded by the reference line and a positive portion of the spectrum defined as the area ($A_{C=C}$) of a peak derived from a polysulfone-derived aromatic group C=C. Similarly, a reference line was drawn at 1711 to 1751 cm$^{-1}$, and the area of a portion surrounded by the reference line and a positive portion of the spectrum defined as the area ($A_{C=O}$) of a peak derived from an ester group. However, depending on the type of carboxylic acid vinyl ester unit and the type of polysulfone-based polymer, the peak may be shifted by about ±10 cm$^{-1}$ and, in this example, the reference line is redrawn as appropriate.

The above-mentioned operation was carried out by performing measurement at three different sites on the same hollow fiber membrane, and calculating the average of ($A_{C=O}/A_{C=C}$), and a value obtained by rounding off the average from the third decimal place was used.

In addition, a reference line was drawn at a peak at 1617 to 1710 cm$^{-1}$, and the area of a portion surrounded by the reference line and a positive portion of the spectrum defined as the area ($A_{N-C=O}$) of a peak derived from an ester group. The above-mentioned operation was carried out by performing measurement at three different sites on the same hollow fiber membrane, and calculating the average of ($A_{N-C=O}/A_{C=C}$), and a value obtained by rounding off the average from the third decimal place was used.

(6) Flat Membrane Platelet Adhesion Test Method

A double-sided tape was bonded to a polystyrene circular plate having a diameter of 18 mm, and a flat membrane cut to 0.5 cm square was fixed thereto. When the surface of the flat membrane has contaminants, scratches, folds and the like, it may be impossible to perform accurate evaluation because platelets adhere to those parts. Therefore, a flat membrane free from contaminants, scratches and folds was used. The circular plate was attached to a cylindrically cut FALCON (registered trademark) tube (18 mm in diameter, No. 2051) such that a surface bonded to the flat membrane was situated inside the cylinder, and a gap was filled with a parafilm. The inside of the cylindrical tube was washed with physiological saline and then filled with physiological saline. Human venous blood was collected, and heparin was then immediately added to 50 U/ml. The physiological saline in the cylindrical tube was discarded, 1.0 ml of the blood then placed in the cylindrical tube and shaken at 37° C. for 1 hour within 10 minutes after collection of the blood. Thereafter, the flat membrane was washed with 10 ml of physiological saline, blood components were immobilized with 2.5% glutaraldehyde physiological saline, and the flat membrane washed with 20 ml of distilled water. The washed flat membrane was dried under reduced pressure at 20° C. and 0.5 Torr for 10 hours. The flat membrane was bonded to a sample stand of a scanning electron microscope with a double-sided tape. Thereafter, a thin membrane of Pt—Pd was formed on the flat membrane surface by sputtering to prepare a sample. The surface of the flat membrane was observed with a field emission type scanning electron microscope (S800 manufactured by Hitachi, Ltd.) at a magnification of 1500 times, and the number of adhering platelets per visual field (4.3×10$^3$ μm$^2$) counted. When 50 or more platelets adhered, the number of adhering platelets was set to 50 with the membrane considered to have no platelet adhesion suppressing effect. The average of the numbers of adhering platelets in 20 different visual fields in the vicinity of the center of the flat membrane was defined as the number of adhering platelets (number/4.3×10$^3$ μm$^2$). When an electron microscope having a different visual field area is used, conversion may be appropriately performed to obtain the number of adhering platelets (number/4.3×10$^3$ μm$^2$).

(7) Measurement of Relative Adhesion Amount of Fibrinogen 4 mL of human fresh blood containing 15% of an ACD-A solution was circulated through the hollow fiber membrane module at a flow rate of 1 mL/min for 1 hour. The hollow fiber membrane module was washed for 20 minutes by feeding a phosphate buffer solution (PBS) therethrough, and a follow fiber then cut out by 10 cm from the mini module, finely cut to an about 2 mm length, and placed in an Eppendorf tube. Washing was performed with PBS (1 mL×3 times, washing was repeated when blood remained). Tween-20 (Katayama Chemical, Ltd) was adjusted to 0.05% by weight with PBS (hereinafter, abbreviated as PBS-T). Skim milk was dissolved in PBS-T in a concentration of 0.1% by weight, and washing performed three times with the solution. An anti-human fibrinogen (HPR) antibody was diluted 10000 times with 0.1% by weight of a skim milk/PBS-T solution, added in an amount of 1 mL, and then rotated and stirred with a rotator at room temperature for 2 hours. Washing was performed twice with 0.1% by weight of the skim milk/PBS-T solution, followed by washing twice with 0.1% by weight of a skim milk/PBS solution. 1 mL of a TMBone solution was added, and stirred with a micro mixer. The reaction was stopped by adding 200 µL of 6N hydrochloric acid with respect to the degree of color development (the reaction is controlled so that the absorbance of a control as described later falls within a range of 1 to 1.5). The absorbance at 450 nm was measured with an absorbance measurement apparatus: Microplate Reader MPR-A4i (manufactured by Tosoh Corporation). From the absorbance (Ac) of the control ("Toraylight" CX) and the absorbance (As) of the target sample, the relative adhesion amount of fibrinogen was determined in accordance with the following formula.

relative adhesion amount (%) of fibrinogen=$As/Ac \times 100$

When the relative adhesion amount of fibrinogen is measured for a membrane other than a hollow fiber membrane, 4 mL of human fresh blood is brought into contact with the functional layer of the sample for 1 hour by a method such as immersion in blood, and the sample washed using a phosphate buffer solution (PBS). Thereafter, the absorbance is measured in the same manner as in the hollow fiber membrane, and the relative adhesion amount of fibrinogen calculated. For the control, a material before immobilization of a polymer containing a saturated aliphatic monocarboxylic acid vinyl ester unit on the functional layer is used.

(8) Antibody Purification Model Test Method 10 mL of human plasma containing 100 mg of IgG (derived from human serum, Oriental Yeast Co., Ltd.) was prepared, and circulated through an antibody purifying separation membrane module for 1 hour at a flow rate of 3 mL/min and a filtration flow rate of 1.5 mL/min with a PBS supply flow rate of 1.5 mL/min. The inner surface of the separation membrane was washed with 5 mL of PBS, and the solution added to plasma after circulation to obtain a recovery solution. The recovery rate of IgG was calculated from (weight of IgG contained in recovery solution)/(weight of IgG contained in initial plasma)×100%. The weight of IgG was calculated by measuring the IgG concentration with an ELISA kit (manufactured by Funakoshi Co., Ltd.) and multiplying the value of the solution amount.

Method of Producing Hollow Fiber Membrane Module 18 parts by weight of polysulfone (Udel P-3500 manufactured by Teijin Amoco Co., Ltd.) and 9 parts by weight of polyvinylpyrrolidone (K30 manufactured by BASF SE) were added to 72 parts by weight of N,N-dimethylacetamide and 1 part by weight of water, and the mixture heated at 90° C. for 14 hours to be dissolved. The film formation dope solution was discharged from an orifice-type double cylindrical die having an outer diameter of 0.3 mm and an inner diameter of 0.2 mm, a solution including 57.5 parts by weight of N,N-dimethylacetamide and 42.5 parts by weight of water was discharged as a core liquid, and after the solution passed over a dry length of 350 mm, the solution was guided to a coagulation bath of 100% water to obtain a hollow fiber membrane. The obtained hollow fiber membrane had an inner diameter of 200 µm and a thickness of 40 µm. 50 hollow fiber membranes were inserted into a plastic tube, and the plastic tube was fixed at both ends with an adhesive to prepare a plastic tube mini module having an effective length of 100 mm. An aqueous solution with the polymer dissolved therein was fed from a blood-side inlet to a dialysate-side inlet of the mini module. Further, a 0.1 wt % ethanol aqueous solution was fed from the blood-side inlet to the dialysate-side inlet and from the blood-side inlet to a blood-side outlet of the hollow fiber membrane module, and a γ-ray of 25 kGy was then applied to obtain a hollow fiber membrane module.

Example 1

A vinylpyrrolidone/vinyl hexanoate random copolymer was prepared by the following method. 16.2 g of a vinylpyrrolidone monomer (Wako Pure Chemical Industries, Ltd.), 20.8 g of a vinyl hexanoate monomer (Tokyo Chemical Industry Co., Ltd.), 56 g of isopropanol (Wako Pure Chemical Industries, Ltd.) as a polymerization solvent, and 0.35 g of azobisdimethylbutyronitrile as a polymerization initiator were mixed, and the mixture stirred at 70° C. for 8 hours under a nitrogen atmosphere. The reaction liquid was cooled to room temperature, and concentrated, and the concentration residue was put in hexane. The precipitated white precipitate was recovered, and dried under reduced pressure at 50° C. for 12 hours to obtain 25.0 g of a vinyl pyrrolidone/vinyl hexanoate random copolymer. The result of $^1$H-NMR measurement showed that the molar fraction of the vinyl hexanoate unit was 40%. The result of GPC measurement showed that the number average molecular weight was 2,200.

A 1.0 wt % ethanol aqueous solution with 300 ppm of the prepared vinylpyrrolidone/vinyl hexanoate random copolymer dissolved therein was fed from a blood-side inlet to a dialysate-side inlet of a hollow fiber membrane module prepared by the method of producing a hollow fiber membrane module. Further, a 0.1 wt % ethanol aqueous solution was fed from the blood-side inlet to the dialysate-side inlet and from the blood-side inlet to a blood-side outlet of the hollow fiber membrane module, and a γ-ray of 25 kGy was then applied to prepare a hollow fiber membrane module.

The results of TOF-SIMS measurement and XPS measurement showed that a hexanoic acid ester was present on the surface of a functional layer of the hollow fiber membrane. In addition, the results of ATR-IR measurement showed that peaks were present in ranges of 1711 to 1751 cm$^{-1}$, 1617 to 1710 cm$^{-1}$ and 1549 to 1620 cm$^{-1}$. The result of ATR-IR measurement showed that the amount of the copolymer immobilized on the inner surface of the hollow fiber membrane (average of the ratio of the area $A_{C=O}$ of a peak in a range of 1711 to 1751 cm$^{-1}$ and the area $A_{C=C}$ of a peak in a range of 1549 to 1620 cm$^{-1}$ ($A_{C=O}/A_{C=C}$)) was 0.03. The relative adhesion amount of fibrinogen to the prepared hollow fiber membrane module was measured. The result of the measurement showed that the relative adhesion amount was 12% as shown in Table 1.

Example 2

A hollow fiber membrane module was prepared in the same manner as in Example 1 except that the concentration of the copolymer during preparation of the hollow fiber membrane module was changed from 300 ppm to 500 ppm.

The results of TOF-SIMS measurement and XPS measurement showed that a hexanoic acid ester was present on the surface of a functional layer of the hollow fiber membrane. In addition, the results of ATR-IR measurement showed that peaks were present in ranges of 1711 to 1751 cm$^{-1}$, 1617 to 1710 cm$^{-1}$ and 1549 to 1620 cm$^{-1}$. The result of ATR-IR measurement showed that the amount of the copolymer immobilized on the inner surface of the hollow fiber membrane (average of the ratio of the area $A_{C=O}$ of a peak in a range of 1711 to 1751 cm$^{-1}$ and the area $A_{C=C}$ of a peak in a range of 1549 to 1620 cm$^{-1}$ ($A_{C=O}/A_{C=C}$)) was 0.08. The relative adhesion amount of fibrinogen to the prepared hollow fiber membrane module was measured. The result of the measurement showed that the relative adhesion amount was 7% as shown in Table 1.

Example 3

A vinylpyrrolidone/vinyl propanoate random copolymer was prepared by the following method. 19.5 g of a vinyl pyrrolidone monomer, 17.5 g of a vinyl propionate monomer, 56 g of t-amyl alcohol as a polymerization solvent and 0.175 g of 2,2'-azobis(2,4-dimethylvaleronitrile) as a polymerization initiator were mixed, and the mixture stirred at 70° C. for 6 hours. The reaction liquid was cooled to room temperature to stop the reaction, concentrated, and then put in hexane. The precipitated white precipitate was recovered, and dried under reduced pressure to obtain 21.0 g of a copolymer.

The result of $^1$H-NMR measurement showed that the molar fraction of the vinyl propanoate unit was 40%. In addition, the result of GPC measurement showed that the number average molecular weight was 16,500.

A hollow fiber membrane module was prepared in the same manner as in Example 1 except that a vinylpyrrolidone/vinyl propanoate random copolymer was used in place of the vinylpyrrolidone/vinyl hexanoate random copolymer.

The results of TOF-SIMS measurement and XPS measurement showed that a propanoic acid ester was present on the surface of a functional layer of the hollow fiber membrane. In addition, the results of ATR-IR measurement showed that peaks were present in ranges of 1711 to 1751 cm$^{-1}$, 1617 to 1710 cm$^{-1}$ and 1549 to 1620 cm$^{-1}$. The amount of the copolymer immobilized on the inner surface of the hollow fiber membrane (average of the ratio of the area $A_{C=O}$ of a peak in a range of 1711 to 1751 cm$^{-1}$ and the area $A_{C=C}$ of a peak in a range of 1549 to 1620 cm$^{-1}$ ($A_{C=O}/A_{C=C}$)) was 0.06. The relative adhesion amount of fibrinogen to the prepared hollow fiber membrane module was measured. The result of the measurement showed that the relative adhesion amount was 5% as shown in Table 1.

Example 4

A hollow fiber membrane module was prepared in the same manner as in Example 1 except that a vinylpyrrolidone/vinyl valerate random copolymer (molar fraction of vinyl valerate unit: 40%, number average molecular weight: 3,900) was used in place of the vinylpyrrolidone/vinyl hexanoate random copolymer.

The results of TOF-SIMS measurement and XPS measurement showed that a valeric acid ester was present on the surface of a functional layer of the hollow fiber membrane. In addition, the results of ATR-IR measurement showed that peaks were present in ranges of 1711 to 1751 cm$^{-1}$, 1617 to 1710 cm$^{-1}$ and 1549 to 1620 cm$^{-1}$. The amount of the copolymer immobilized on the inner surface of the hollow fiber membrane (average of the ratio of the area $A_{C=O}$ of a peak in a range of 1711 to 1751 cm$^{-1}$ and the area $A_{C=C}$ of a peak in a range of 1549 to 1620 cm$^{-1}$ ($A_{C=O}/A_{C=C}$)) was 0.02. The relative adhesion amount of fibrinogen to the prepared hollow fiber membrane module was measured, and the result showed that the relative adhesion amount was 25% as shown in Table 1.

Example 5

A hollow fiber membrane module was prepared in the same manner as in Example 1 except that 100 ppm of a vinylacetamide/vinyl pivalate random copolymer (molar fraction of vinyl pivalate unit: 50%, number average molecular weight: 7,700) was used in place of 300 ppm of the vinylpyrrolidone/vinyl hexanoate random copolymer.

The results of TOF-SIMS measurement and XPS measurement showed that a pivalic acid ester was present on the surface of a functional layer of the hollow fiber membrane. In addition, the results of ATR-IR measurement showed that peaks were present in ranges of 1711 to 1751 cm$^{-1}$, 1617 to 1710 cm$^{-1}$ and 1549 to 1620 cm$^{-1}$. The amount of the copolymer immobilized on the inner surface of the hollow fiber membrane (average of the ratio of the area $A_{C=O}$ of a peak in a range of 1711 to 1751 cm$^{-1}$ and the area $A_{C=C}$ of a peak in a range of 1549 to 1620 cm$^{-1}$ ($A_{C=O}/A_{C=C}$)) was 0.06. The relative adhesion amount of fibrinogen to the prepared hollow fiber membrane module was measured, and the result showed that the relative adhesion amount was 9% as shown in Table 1.

Comparative Example 1

A hollow fiber membrane module was prepared in the same manner as in Example 1 except that polyvinylpyrrolidone ("K90" manufactured by BASF SE) was used in place of the vinylpyrrolidone/vinyl hexanoate random copolymer.

The results of TOF-SIMS measurement and XPS measurement showed that a carboxylic acid ester was not present on the surface of a functional layer of the hollow fiber membrane. In addition, the results of ATR-IR measurement showed that peaks were present in ranges of 1617 to 1710 cm$^{-1}$ and 1549 to 1620 cm$^{-1}$, but a peak was not present in a range of 1711 to 1751 cm$^{-1}$. The relative adhesion amount of fibrinogen to the prepared hollow fiber membrane module was measured. The result of the measurement showed that the relative adhesion amount was 90% as shown in Table 1.

Comparative Example 2

A hollow fiber membrane module was prepared in the same manner as in Example 1 except that a vinylpyrrolidone/vinyl acetate random copolymer ("Kollidon VA64" manufactured by BASF SE) was used in place of the vinylpyrrolidone/vinyl hexanoate random copolymer. The results of TOF-SIMS measurement and XPS measurement showed that an acetic acid ester was present on the surface of a functional layer of the hollow fiber membrane.

In addition, the results of ATR-IR measurement showed that peaks were present in ranges of 1711 to 1751 cm$^{-1}$, 1617 to 1710 cm$^{-1}$ and 1549 to 1620 cm$^{-1}$. It was shown that the amount of the copolymer immobilized on the inner surface of the hollow fiber membrane (average of the ratio of the area $A_{C=O}$ of a peak in a range of 1711 to 1751 cm$^{-1}$ and the area $A_{C=C}$ of a peak in a range of 1549 to 1620 cm$^{-1}$ ($A_{C=O}/A_{C=C}$)) was 0.04. The relative adhesion amount of fibrinogen to the prepared hollow fiber membrane module was measured, and the result showed that the relative adhesion amount was 60% as shown in Table 1.

Comparative Example 3

A hollow fiber membrane module was prepared in the same manner as in Example 1 except that a vinylpyrrolidone/vinyl acetate random copolymer ("Kollidon VA64" manufactured by BASF SE) was used in place of the vinylpyrrolidone/vinyl hexanoate random copolymer, the concentration of the copolymer during preparation of the hollow fiber membrane module was changed from 300 ppm to 1000 ppm, and water was used thoroughly in place of the 0.1 wt % ethanol aqueous solution.

The results of TOF-SIMS measurement and XPS measurement showed that an acetic acid ester was present on the surface of a functional layer of the hollow fiber membrane. In addition, the results of ATR-IR measurement showed that peaks were present in ranges of 1711 to 1751 cm$^{-1}$, 1617 to 1710 cm$^{-1}$ and 1549 to 1620 cm$^{-1}$. The amount of the copolymer immobilized on the inner surface of the hollow fiber membrane (average of the ratio of the area $A_{C=O}$ of a peak in a range of 1711 to 1751 cm$^{-1}$ and the area $A_{C=C}$ of a peak in a range of 1549 to 1620 cm$^{-1}$ ($A_{C=O}/A_{C=C}$)) was 0.12. The relative adhesion amount of fibrinogen to the prepared hollow fiber membrane module was measured, and the result showed that the relative adhesion amount was 65% as shown in Table 1.

Comparative Example 4

A 1.0 wt % ethanol aqueous solution was fed from a blood-side inlet to a dialysate-side inlet of a hollow fiber membrane module prepared by the method of producing a hollow fiber membrane module. Next, a 0.1 wt % ethanol aqueous solution was fed from the blood-side inlet to the dialysate-side inlet and from the blood-side inlet to a blood-side outlet of the hollow fiber membrane module, and a γ-ray of 25 kGy was then applied to prepare a hollow fiber membrane module.

The results of TOF-SIMS measurement and XPS measurement showed that a carboxylic acid ester was not present on the surface of a functional layer of the hollow fiber membrane. In addition, the results of ATR-IR measurement showed that peaks were present in ranges of 1617 to 1710 cm$^{-1}$ and 1549 to 1620 cm$^{-1}$, but a peak was not present in a range of 1711 to 1751 cm$^{-1}$. The relative adhesion amount of fibrinogen to the prepared hollow fiber membrane module was measured, and the result showed that the relative adhesion amount was 110% as shown in Table 1.

Comparative Example 5

A hollow fiber membrane module was prepared in the same manner as in Comparative Example 4 except that a 1.0 wt % hexanol aqueous solution was used thoroughly in place of the 1.0 wt % ethanol aqueous solution.

The results of TOF-SIMS measurement and XPS measurement showed that a carboxylic acid ester was not present on the surface of a functional layer of the hollow fiber membrane. In addition, the results of ATR-IR measurement showed that peaks were present in ranges of 1617 to 1710 cm$^{-1}$ and 1549 to 1620 cm$^{-1}$, but a peak was not present in a range of 1711 to 1751 cm$^{-1}$. The relative adhesion amount of fibrinogen to the prepared hollow fiber membrane module was measured, and the result showed that the relative adhesion amount was 73% as shown in Table 1.

Comparative Example 6

A hollow fiber membrane module was prepared in the same manner as in Example 1 except that a vinylpyrrolidone/vinyl acetate block copolymer (molar fraction of vinyl acetate unit: 40%, number average molecular weight: 4,600) was used in place of the vinylpyrrolidone/vinyl hexanoate random copolymer, and the concentration of the copolymer during preparation of the hollow fiber membrane module was changed from 300 ppm to 30 ppm.

The results of TOF-SIMS measurement and XPS measurement showed that an acetic acid ester was present on the surface of a functional layer of the hollow fiber membrane. In addition, the results of ATR-IR measurement showed that peaks were present in ranges of 1711 to 1751 cm$^{-1}$, 1617 to 1710 cm$^{-1}$ and 1549 to 1620 cm$^{-1}$. The amount of the copolymer immobilized on the inner surface of the hollow fiber membrane (average of the ratio of the area $A_{C=O}$ of a peak in a range of 1711 to 1751 cm$^{-1}$ and the area $A_{C=C}$ of a peak in a range of 1549 to 1620 cm$^{-1}$ ($A_{C=O}/A_{C=C}$)) was 0.04. The relative adhesion amount of fibrinogen to the prepared hollow fiber membrane module was measured, and the result showed that the relative adhesion amount was 83% as shown in Table 1.

TABLE 1

| | Saturated aliphatic monocarboxylate ion | Area percentage of carbon peak derived from ester group (atomic %) | Immobilized polymer | Molar fraction of saturated aliphatic monocarboxylic acid vinyl ester (%) | Average of $A_{C=O}/A_{C=C}$ | Average of $A_{N-C=O}/A_{C=C}$ | Relative adhesion amount of fibrinogen (%) |
|---|---|---|---|---|---|---|---|
| Example 1 | Hexanoate ion | 1.0 | Vinylpyrrolidone/vinyl hexanoate random copolymer | 40 | 0.03 | 1.14 | 12 |
| Example 2 | Hexanoate ion | 2.6 | Vinylpyrrolidone/vinyl hexanoate random copolymer | 40 | 0.08 | 1.12 | 7 |
| Example 3 | Propanoate ion | 2.5 | Vinylpyrrolidone/vinyl propanoate random copolymer | 40 | 0.06 | 1.16 | 5 |
| Example 4 | Valerate ion | 0.7 | Vinylpyrrolidone/vinyl valerate random copolymer | 40 | 0.02 | 1.04 | 25 |
| Example 5 | Pivalate ion | 2.9 | Vinylacetamide/vinyl pivalate random copolymer | 50 | 0.06 | 1.10 | 9 |

TABLE 1-continued

|  | Saturated aliphatic monocarboxylate ion | Area percentage of carbon peak derived from ester group (atomic %) | Immobilized polymer | Molar fraction of saturated aliphatic monocarboxylic acid vinyl ester (%) | Average of $A_{C=O}/A_{C=C}$ | Average of $A_{N-C=O}/A_{C=C}$ | Relative adhesion amount of fibrinogen (%) |
|---|---|---|---|---|---|---|---|
| Comparative Example 1 | — | — | Polyvinylpyrrolidone | 0 | — | 1.20 | 90 |
| Comparative Example 2 | Acetate ion | 2.2 | Vinylpyrrolidone/vinyl acetate random copolymer | 40 | 0.04 | 1.15 | 60 |
| Comparative Example 3 | Acetate ion | 3.0 | Vinylpyrrolidone/vinyl acetate random copolymer | 40 | 0.12 | 1.20 | 65 |
| Comparative Example 4 | — | — | — | — | — | — | 110 |
| Comparative Example 5 | — | — | — | — | — | — | 73 |
| Comparative Example 6 | Acetate ion | 1.0 | Vinylpyrrolidone/vinyl acetate block copolymer | 40 | 0.04 | 1.15 | 83 |

Method of Producing Flat Membrane

The polymer was dissolved in chloroform (Wako Pure Chemical Industries, Ltd.), and the concentration adjusted to 1% by weight. 1 mL of the polymer solution was dropped onto a glass slide having a diameter of 2 cm, and naturally dried at 20° C. for 1 hour. By irradiating a γ-ray (25 kGy), the polymer was crosslinked and immobilized on the glass surface to obtain a flat membrane.

Example 6

A flat membrane was prepared by the method of producing a flat membrane using a polyvinyl propanoate homopolymer (number average molecular weight: 15,500) as the polymer.

TOF-SIMS measurement and XPS measurement of the obtained flat membrane were performed, and the result showed that a propanoic acid ester was present. A platelet adhesion test was conducted, and the result showed that as shown in Table 2, the number of adhering platelets was 6, and adhesion of platelets was considerably suppressed.

Example 7

A flat membrane was prepared by the method of producing a flat membrane using a vinylpyrrolidone/vinyl decanoate random copolymer (molar fraction of decanoic acid vinyl unit: 40%, number average molecular weight: 35,000) as the polymer.

TOF-SIMS measurement and XPS measurement of the obtained flat membrane were performed, and the result showed that a decanoic acid ester was present. A platelet adhesion test was conducted, and the result showed that as shown in Table 2, the number of adhering platelets was 11, and adhesion of platelets was considerably suppressed.

Example 8

A flat membrane was prepared by the method of producing a flat membrane using a vinylpyrrolidone/vinyl hexanoate random copolymer (molar fraction of hexanoic acid vinyl unit: 40%, number average molecular weight: 2,200) as the polymer.

TOF-SIMS measurement and XPS measurement of the obtained flat membrane were performed, and the result showed that a hexanoic acid ester was present. A platelet adhesion test was conducted, and the result showed that as shown in Table 2, the number of adhering platelets was 0, and adhesion of platelets was considerably suppressed.

Example 9

A flat membrane was prepared by the method of producing a flat membrane using a vinylpyrrolidone/vinyl propanoate random copolymer (molar fraction of propanoic acid vinyl unit: 40%, number average molecular weight: 16,500) as the polymer.

TOF-SIMS measurement and XPS measurement of the obtained flat membrane were performed, and the result showed that a propanoic acid ester was present. A platelet adhesion test was conducted, and the result showed that as shown in Table 2, the number of adhering platelets was 1, and adhesion of platelets was considerably suppressed.

Example 10

A flat membrane was prepared by the method of producing a flat membrane using a vinylacetamide/vinyl pivalate random copolymer (molar fraction of pivalic acid vinyl unit: 30%, number average molecular weight: 5,500) as the polymer.

TOF-SIMS measurement and XPS measurement of the obtained flat membrane were performed, and the result showed that a pivalic acid ester was present. A platelet adhesion test was conducted, and the result showed that as shown in Table 2, the number of adhering platelets was 2, and adhesion of platelets was considerably suppressed.

Comparative Example 7

A platelet adhesion test was conducted on an untreated glass slide on which a polymer was not immobilized.

The result showed that the number of adhering platelets was 50 as shown in Table 2.

Comparative Example 8

A flat membrane was prepared by the method of producing a flat membrane using polyvinylpyrrolidone ("K30" manufactured by BASF SE) as the polymer.

TOF-SIMS measurement and XPS measurement of the obtained flat membrane were performed, and the result showed that a carboxylic acid ester was not present. A platelet adhesion test was conducted, and the result showed that the number of adhering platelets was 47, and adhesion of platelets was not suppressed.

Comparative Example 9

A flat membrane was prepared by the method of producing a flat membrane using a vinylpyrrolidone/vinyl acetate random copolymer (molar fraction of acetic acid vinyl unit: 20%, number average molecular weight: 3,200) as the polymer.

TOF-SIMS measurement and XPS measurement of the obtained flat membrane were performed, and the result showed that an acetic acid ester was present. A platelet adhesion test was conducted, and the result showed that the number of adhering platelets was 43, and adhesion of platelets was not suppressed.

brane (average of the ratio of the area $A_{C=O}$ of a peak in a range of 1711 to 1751 cm$^{-1}$ and the area $A_{C=C}$ of a peak in a range of 1549 to 1620 cm$^{-1}$ ($A_{C=O}/A_{C=C}$)) was 0.01. An antibody purification model test was conducted, and the result showed that the IgG recovery rate was 70%.

Comparative Example 10

A solution of a polymer was not fed, and a γ-ray of 25 kGy applied to prepare a separation membrane module. TOF-SIMS measurement and XPS measurement of the obtained separation membrane were performed, and the result showed that a carboxylic acid ester was not present. An antibody purification model test was conducted, and the result showed that the IgG recovery rate was 45%.

TABLE 2

| | Saturated aliphatic monocarboxylate ion | Area percentage of carbon peak derived from ester group (atomic %) | Immobilized polymer | Molar fraction of saturated aliphatic monocarboxylic acid vinyl ester (%) | Number of adhering platelets |
|---|---|---|---|---|---|
| Example 6 | Propanoate ion | 20.1 | Polyvinyl propanoate homopolymer | 100 | 6 |
| Example 7 | Decanoate ion | 4.8 | Vinylpyrrolidone/vinyl decanoate random copolymer | 40 | 11 |
| Example 8 | Hexanoate ion | 5.9 | Vinylpyrrolidone/vinyl hexanoate random copolymer | 40 | 0 |
| Example 9 | Propanoate ion | 7.1 | Vinylpyrrolidone/vinyl propanoate random copolymer | 40 | 1 |
| Example 10 | Vinyl pivalate | 3.2 | Vinyl acetamide/vinyl pivalate random copolymer | 30 | 2 |
| Comparative Example 7 | — | — | — | — | 50 |
| Comparative Example 8 | — | — | Polyvinylpyrrolidone | 0 | 47 |
| Comparative Example 9 | Acetate ion | 7.7 | Vinylpyrrolidone/vinyl acetate random copolymer | 20 | 43 |

Method of Producing Antibody Purifying Separation Membrane Module

A separation membrane module was prepared in the same manner as in the method of producing a hollow fiber membrane module except that the core liquid was changed to 65 parts by weight of N,N-dimethylacetamide and 35 parts by weight of water.

Example 11

A 0.1 wt % ethanol aqueous solution with 50 ppm of a vinylpyrrolidone/vinyl propanoate random copolymer (molar fraction of vinyl propanoate unit: 20%, number average molecular weight: 12,500) dissolved therein was fed from a blood-side inlet to a dialysate-side inlet of a separation membrane module prepared by the method of producing an antibody purifying separation membrane module. Thereafter, a γ-ray of 25 kGy was applied to prepare a separation membrane module.

The results of TOF-SIMS measurement and XPS measurement showed that a propanoic acid ester was present on the surface of a functional layer of the separation membrane. In addition, the results of ATR-IR measurement showed that peaks were present in ranges of 1711 to 1751 cm$^{-1}$, 1617 to 1710 cm$^{-1}$ and 1549 to 1620 cm$^{-1}$. The result of ATR-IR measurement showed that the amount of the copolymer immobilized on the inner surface of the separation mem-

INDUSTRIAL APPLICABILITY

The biological component adhesion-suppressing material is excellent in biocompatibility, and capable of suppressing adhesion of biological components such as platelets and proteins and, therefore, can be suitably used as a medical material, or a separation material or analytical material for biological components. The bioadhesion-suppressing material can be used for a long period of time due to suppression of adhesion of biological components and, therefore, can be suitably used as a material for a blood purifier.

The invention claimed is:

1. A biological component adhesion-suppressing material comprising:
   a substrate having a functional layer with a polymer immobilized on a surface that is suitable for contact with a biological component, the polymer containing a saturated aliphatic monocarboxylic acid vinyl ester unit,
   wherein the polymer is a copolymer,
   a molar fraction of the saturated aliphatic monocarboxylic acid vinyl ester in the copolymer containing the saturated aliphatic monocarboxylic acid vinyl ester is 30% or more and 50% or less,
   the number of carbon atoms in an aliphatic chain in a saturated aliphatic monocarboxylic acid ion signal detected in compositional analysis of the surface of the functional layer by a TOF-SIMS apparatus is 2 to 20, and a peak derived from an ester group is present in XPS measurement of the surface of the functional layer.

2. The biological component adhesion-suppressing material according to claim 1, wherein the saturated aliphatic monocarboxylic acid ion signal is derived from a copolymer containing a saturated aliphatic monocarboxylic acid vinyl ester, and has antithrombogenicity.

3. The biological component adhesion-suppressing material according to claim 1, wherein the number of carbon atoms in an aliphatic chain in the saturated aliphatic monocarboxylic acid ion signal is 2 to 9.

4. The biological component adhesion-suppressing material according to claim 1, wherein, in XPS measurement of the surface of the functional layer, the area percentage of the carbon peak derived from an ester group is 0.5 to 25 (atomic %) where the total area of peaks derived from carbon is 100 (atomic %).

5. The biological component adhesion-suppressing material according to claim 1, wherein, in ATR-IR measurement of the surface of the functional layer, a peak is present in each of both a range of 1711 to 1751 $cm^{-1}$ and a range of 1549 to 1620 $cm^{-1}$, and the average of the ratio of the peak area $A_{C=O}$ in the range of 1711 to 1751 $cm^{-1}$ to the peak area $A_{C=C}$ in the range of 1549 to 1620 $cm^{-1}$ ($A_{C=O}/A_{C=C}$) is 0.01 to 1.0.

6. The biological component adhesion-suppressing material according to claim 5, wherein the peak present in the range of 1549 to 1620 $cm^{-1}$ is derived from aromatic groups in a polysulfone-based polymer.

7. The biological component adhesion-suppressing material according to claim 5, wherein a peak is present in a range of 1617 to 1710 $cm^{-1}$ in ATR-IR measurement of the surface of the functional layer.

8. The biological component adhesion-suppressing material according to claim 7, wherein the peak present in the range of 1617 to 1710 $cm^{-1}$ indicates the presence of an amide bond in a hydrophilic polymer containing a vinylpyrrolidone unit, a vinylcaprolactam unit, a vinylacetamide unit or an acrylamide unit.

9. The biological component adhesion-suppressing material according to claim 1, used for blood purification.

10. A blood purifier comprising the biological component adhesion-suppressing material according to claim 1.

11. The biological component adhesion-suppressing material according to claim 2, wherein the number of carbon atoms in an aliphatic chain in the saturated aliphatic monocarboxylic acid ion signal is 2 to 9.

12. The biological component adhesion-suppressing material according to claim 2, wherein, in XPS measurement of the surface of the functional layer, the area percentage of the carbon peak derived from an ester group is 0.5 to 25 (atomic %) where the total area of peaks derived from carbon is 100 (atomic %).

13. The biological component adhesion-suppressing material according to claim 3, wherein, in XPS measurement of the surface of the functional layer, the area percentage of the carbon peak derived from an ester group is 0.5 to 25 (atomic %) where the total area of peaks derived from carbon is 100 (atomic %).

14. The biological component adhesion-suppressing material according to claim 2, wherein, in ATR-IR measurement of the surface of the functional layer, a peak is present in each of both a range of 1711 to 1751 $cm^{-1}$ and a range of 1549 to 1620 $cm^{-1}$, and the average of the ratio of the peak area $A_{C=O}$ in the range of 1711 to 1751 $cm^{-1}$ to the peak area $A_{C=C}$ in the range of 1549 to 1620 $cm^{-1}$ ($A_{C=O}/A_{C=C}$) is 0.01 to 1.0.

15. The biological component adhesion-suppressing material according to claim 3, wherein, in ATR-IR measurement of the surface of the functional layer, a peak is present in each of both a range of 1711 to 1751 $cm^{-1}$ and a range of 1549 to 1620 $cm^{-1}$, and the average of the ratio of the peak area $A_{C=O}$ in the range of 1711 to 1751 $cm^{-1}$ to the peak area $A_{C=C}$ in the range of 1549 to 1620 $cm^{-1}$ ($A_{C=O}/A_{C=C}$) is 0.01 to 1.0.

16. The biological component adhesion-suppressing material according to claim 4, wherein, in ATR-IR measurement of the surface of the functional layer, a peak is present in each of both a range of 1711 to 1751 $cm^{-1}$ and a range of 1549 to 1620 $cm^{-1}$, and the average of the ratio of the peak area $A_{C=O}$ in the range of 1711 to 1751 $cm^{-1}$ to the peak area $A_{C=C}$ in the range of 1549 to 1620 $cm^{-1}$ ($A_{C=O}/A_{C=C}$) is 0.01 to 1.0.

17. The biological component adhesion-suppressing material according to claim 6, wherein a peak is present in a range of 1617 to 1710 $cm^{-1}$ in ATR-IR measurement of the surface of the functional layer.

18. The biological component adhesion-suppressing material according to claim 2, used for blood purification.

19. The biological component adhesion-suppressing material according to claim 3, used for blood purification.

20. The biological component adhesion-suppressing material according to claim 4, used for blood purification.

21. The biological component adhesion-suppressing material according to claim 1, wherein a monomer to be copolymerized with the saturated aliphatic monocarboxylic acid vinyl ester is a hydrophilic monomer.

22. A blood circuit, a blood storage bag, a catheter, a stent, a contact lens, or a blood glucose level sensor comprising the biological component adhesion-suppressing material according to claim 1.

* * * * *